Figure 1:
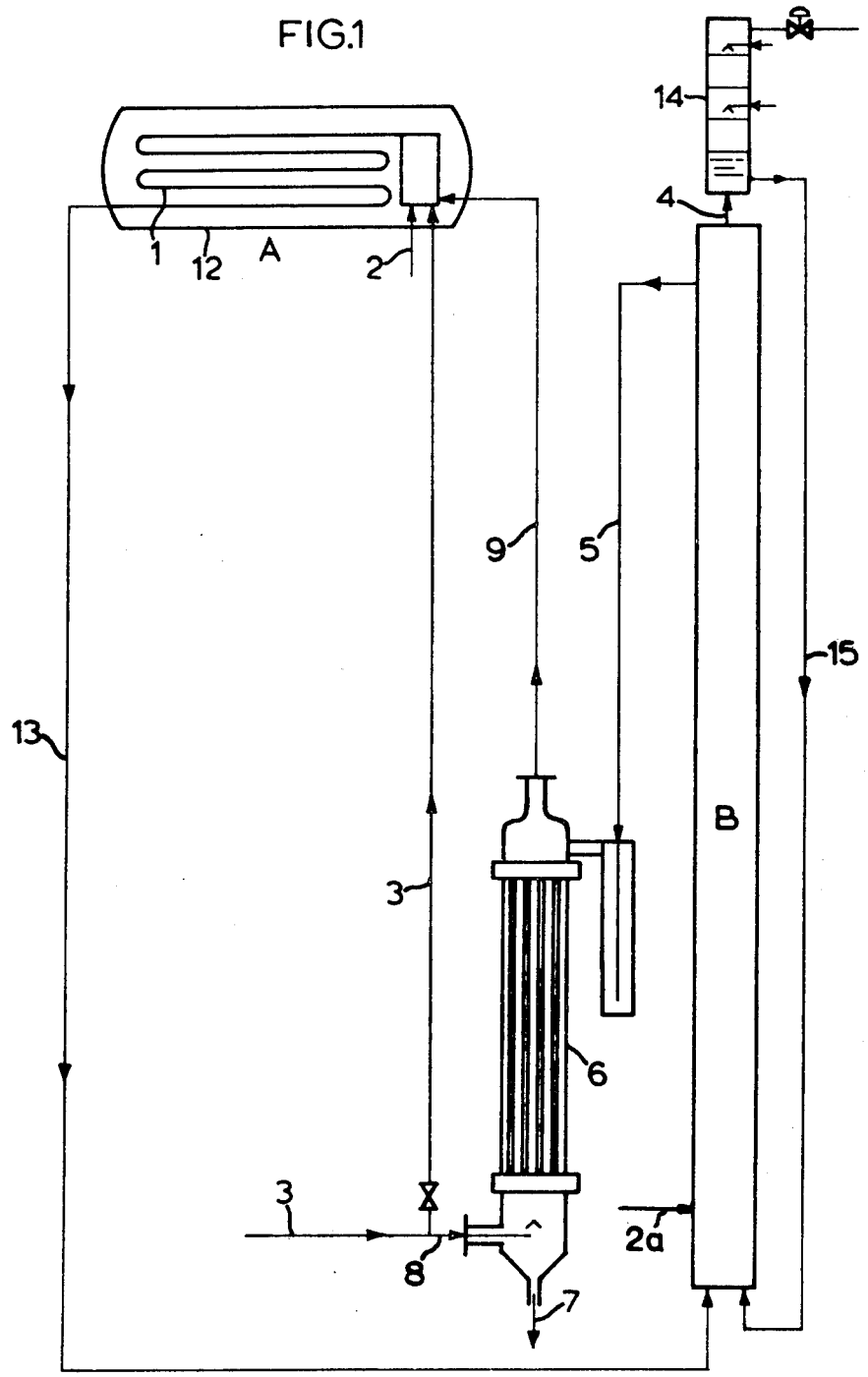

United States Patent [19]

Kaasenbrood

[11] 4,001,320
[45] Jan. 4, 1977

[54] METHOD FOR CONTROLLING THE AMMONIA AND $CO_2$ RATIOS IN A UREA MANUFACTURING PROCESS

[75] Inventor: Petrus J. C. Kaasenbrood, Sittard, Netherlands

[73] Assignee: Stamicarbon, B.V., Geleen, Netherlands

[22] Filed: May 13, 1975

[21] Appl. No.: 577,015

Related U.S. Application Data

[63] Continuation of Ser. No. 41,163, May 25, 1970, abandoned, which is a continuation of Ser. No. 631,335, April 17, 1967, abandoned, which is a continuation-in-part of Ser. No. 531,833, March 4, 1966, Pat. No. 3,356,723, which is a continuation-in-part of Ser. No. 100,339, April 13, 1961, abandoned.

[30] Foreign Application Priority Data

Apr. 22, 1966 Netherlands ...................... 6605483

[52] U.S. Cl. .......................... 260/555 A; 23/232 C
[51] Int. Cl.² .......................................... C07C 126/00
[58] Field of Search ............... 260/555 A; 23/232 C

[56] References Cited

UNITED STATES PATENTS

| | | | |
|---|---|---|---|
| 3,026,184 | 3/1962 | Karasek | 23/232 C |
| 3,304,159 | 2/1967 | Hinsvark | 23/232 C |
| 3,372,189 | 3/1968 | Otsuka et al. | 260/555 A |

FOREIGN PATENTS OR APPLICATIONS 690,618   7/1964   Canada ............................ 260/555

*Primary Examiner*—Oscar R. Vertiz
*Assistant Examiner*—Eugene T. Wheelock
*Attorney, Agent, or Firm*—Cushman, Darby & Cushman

[57] ABSTRACT

A process for urea manufacture is described wherein the molar ratio of unreacted $NH_3$ to $CO_2$ (including $NH_3$ and $CO_2$ in the form of ammonium carbamate) in the carbamate reaction liquid phase is between 2:1 and 3:1, and the same ratio in the liquid phase in the urea autoclave is maintained between 3:1 and 6:1, control of the process being achieved by analysis of the gas phase and maintaining the $NH_3$ to $CO_2$ molar ratio therein between about 1:1 and 6:1, preferably between about 1.5:1 and 3.5:1, in both the carbamate reactor and the urea autoclave.

2 Claims, 2 Drawing Figures

METHOD FOR CONTROLLING THE AMMONIA AND CO₂ RATIOS IN A UREA MANUFACTURING PROCESS

This is a continuation of application Ser. No. 41,163 filed May 25, 1970, now abandoned which is a continuation of Ser. No. 631,335, now abandoned filed Apr. 17, 1967, which is a continuation-in-part of Ser. No. 531,833, filed Mar. 4, 1966, now U.S. Pat. No. 3,356,723 which was, in turn, a continuation-in-part of U.S. Ser. No. 100,339, filed Apr. 3, 1961, now abandoned.

BRIEF DESCRIPTION OF THE INVENTION

This invention relates to the manufacture of urea from ammonia and carbon dioxide, and provides an improvement to such processes whereby a more readily controlled and efficient process is achieved.

BACKGROUND OF THE INVENTION

It is well known that the urea may be manufactured by interacting ammonia and carbon dioxide under suitable conditions of heat and pressure to form ammonium carbamate. Subsequently, the ammonium carbamate is decomposed to form urea. Many, many variations of this basic scheme have been proposed in commercial installations, and such systems have been much improved in recent years. The technology has reached the point wherein the practical success and value of a given urea process is dependent upon its near optimum utilization of energy input and conversion of the ammonia feed to urea. Successful systems thus generally require adequate recycle of unconverted ammonia and carbon dioxide in as efficient a manner as possible. At the same time, undesirable by-product formation, especially biuret, must be avoided.

It can be appreciated, of course, that in a process such as urea manufacture wherein there is involved a highly exothermic reaction and a high temperature liquid-gas system of highly corrosive nature, adequate control of the plant is of prime importance. This means that methods have to be developed whereby control of the reaction is achieved as effectively as possible.

The invention thus particularly relates to a method of control and analysis for the kind of urea process, already known, wherein $NH_3$ and $CO_2$ are allowed to react with each other under suitable pressure and reaction conditions to form first a urea reactant solution or 'melt'. This melt contains urea, ammonium carbamate, as well as free $NH_3$ and $CO_2$. Thereafter the ammonium carbamate and ammonia and carbon dioxide components are substantially removed from said solution as a gaseous $NH_3-CO_2$ mixture. This gas removal is effected by stripping the said solution with for example $CO_2$, with simultaneous heating, and at a relatively elevated pressure of from about 50 atm. up to the urea formation pressure. Thereafter, the evolved stripped gas mixture, containing $NH_3$ and $CO_2$, is subjected to the ammonium carbamate-forming reaction conditions and the additional carbamate thus formed is next again subjected to the urea forming reaction conditions. By this means, the $NH_3$ and $CO_2$ content of the urea reactant solution or melt, which had not formed urea, is recovered and converted into additional urea.

DESCRIPTION OF FIG. 1, ILLUSTRATING THE PRIOR ART

Processes of the nature to which this invention is directed are generally illustrated in FIG. 1 of the accompanying drawings.

In FIG. 1, an ammonium carbamate reactor A, consisting of a tube system (1) installed in a pressure vessel (12), and a urea formation autoclave B are connected by a conduit (13). The carbamate reactor may also be installed inside the urea formation autoclave B. The installation further comprises a stripping column (6) and a washing column (14).

When using this installation, it is generally preferred to feed liquid $NH_3$ via conduits (2) and ($2^a$) and $CO_2$ via conduits (3) and (8), and stripping column (6) and conduit (9), under the urea formation pressure, to the tube system (1) of carbamate reactor (A). In this tube system, the $NH_3$ and $CO_2$ feeds are reacted to form an ammonium carbamate melt, the heat produced being carried away, with formation of steam, by water present in pressure vessel (12). The conversion of $NH_3$ and $CO_2$ to ammonium carbamate is then substantially complete and proceeds at a fast rate.

The carbamate melt thus formed, which also contains some urea produced by transformation of ammonium carbamate into urea and water, flows through conduit (13) to the urea formation autoclave B, where further conversion of the ammonium carbamate into urea and water takes place. As is well known, this conversion is an equilibrium reaction in which a portion of the ammonium carbamate, generally about 45–60%, is converted into urea and water, depending on the temperature and pressure conditions, and on the molar $NH_3/CO_2$ ratio on the reaction mixture. As a result, the urea solution discharged from the urea formation autoclave B via conduit (5) still contains considerable quantities of dissolved $NH_3$ and $CO_2$, essentially in the form of ammonium carbamate. To remove this $NH_3$ and $CO_2$, the urea solution is supplied under the urea formation pressure to the top of the stripping column (6), in which it descends as a film along the inner walls of the tubes countercurrent an ascending $CO_2$ gas stream which is continuously supplied via conduits (3) and (8).

The tubes in the stripping column are heated by steam around the tubes. Owing to the resulting heating of the urea solution in the tubes, and to the action of the countercurrent $CO_2$ gas feed, a large portion, circa 90%, of the unreacted ammonia and carbon dioxide content of said solution is stripped off and carried away in the gaseous phase leaving stripping column (6) via conduit (9). These outgoing stripped gases are thus delivered to the ammonium carbamate reactor A via conduit (9), the stripped urea solution being withdrawn from the reactor base (6) via conduit (7).

By then expanding said urea solution to a much lower pressure, the remainder of dissolved unreacted $NH_3-CO_2$ gas mixture can be expelled from it. These gases are then preferably absorbed in water and the ammonium carbamate solution so formed can be resupplied as washing liquid to the top of washing column (14).

The $CO_2$ used in this process as the starting material invariably contains some quantity of inert gases, and these must be vented in the aforesaid installation. These gases to be vented flow through conduit (4) into the base of washing column (14), where $NH_3$ and $CO_2$ entrained by the vent gases are absorbed in the washing liquid. The washing solution thus formed is then fed into the base of urea formation autoclave B via conduit (15).

The reaction of $NH_3$ and $CO_2$ to form ammonium carbamate, and the subsequent conversion of ammonium carbamate into urea and water, can be quite readily effected at a higher pressure than the stripping treatment in the stripping column (6). It is more attractive, however, on constructional ground, grounds, conduct all these operations at the same pressure, since in that case pumps are not required to bring the stripped gas discharge up to synthesis pressure. However, the problem then arises that, on the one hand, the pressure, and hence the temperature, in the stripping column must not be too high, because otherwise the urea solution from conduit (7) will develop an inadmissibly high biuret content (since the urea decomposes into biuret and ammonium at elevated temperatures). At the same time, the pressure and temperature conditions in the urea formation autoclave must be high enough to cause sufficiently rapid formation of urea from the ammonium carbamate so that an excessively large reactor space will not be required. It is, therefore, essential that, at a given pressure, the temperature of the carbamte melt be more or less optimum, since the rate at which the ammonium carbamate is converted to urea and water will then also be very nearly optimum.

It is also important that in the formation of an ammonium carbamate melt from $NH_3$ and $CO_2$ at a given pressure, this reaction be effected at the highest possible temperature level, since the reaction heat can be used to produce steam of higher temperature levels (and this is important to the over-all economics of the process).

Thus, a very complicated and highly interrelated system of temperatures and pressures must be established and maintained in a fully satisfactory urea synthesis plant. It is the principal object of this invention to provide a novel technique whereby this can be accomplished.

GENERAL DESCRIPTION OF THE INVENTION

It has now been found that in the above-described urea process, the desired temperature conditions can be easily established provided that the molar ratio between still dissolved $NH_3$ and dissolved $CO_2$ in the liquid phase participating in the reaction is between 2:1 and 6:1, the optimum ratio within this range being dependent on the pressure level and the quantity of solvent that is present. In the process here considered, the ratio in the actual urea formation reactor depends on the amounts of urea and water. The higher the pressure level and the larger the amount of solvent that is present in the liquid phase, the higher the molar $NH_3/CO_2$ ratio may be.

The molar ratio herein referred to relates to all the dissolved $NH_3$ and $CO_2$, including all $NH_3$ and $CO_2$ present in the solution in either the free state or, in chemically bonded state other than urea or biuret (e.g., as ammonium carbamate).

For example, to maintain an optimum temperature of 185° C in the urea formation reactor at an operational pressure of 110-150 atm. and at an available amount of solvent (urea + water) equalling 50% of the total liquid phase, in accordance with this invention, the molar ratio between dissolved $NH_3$ and $CO_2$ should be approximately 4.8:1; while in the formation of an ammonium carbamate melt from $NH_3$ and $CO_2$ at a pressure of approximately 125 atm. in the absence of water and/or urea, the molar ratio will have to be adjusted to approximately 2.35:1, to maintain an optimum temperature of about 162° C.

In order that the urea-production process can be kept under control, it is desirable therefore to check each of these molar ratios of the liquid phases participating in the reaction, and to keep each of them at the desired values by controlling the addition of $NH_3$ and $CO_2$. Analyzing these liquid phases is a laborious operation, and even only minor deviations from the desired molar $NH_3/CO_2$ ratio are already known to cause large temperature deviations. Controlling the urea process on the basis of an analysis of the liquid phases is, therefore, not easy to realize in practice.

It has now been found, however, that this process control can be very readily performed by analysis of the gas phase that is in contact with the liquid.

By means of the techniques of gas chromatography, the gas phase can be analyzed in only a few minutes, and in this manner far more rapid analytical reports for process control are available.

It has furthermore also now been found that the results of such a gas phase analysis permit a far better and more sensitive control of the process than can be achieved on the basis of a liquid phase analysis. That is, it is observed that only rather slight deviations from the desired $NH_3/CO_2$ ratio in the liquid phase actually correlate with much larger deviations in the ratio in the gas phase composition. It is thus surprising to note that, notwithstanding the differences arising between the molar $NH_3/CO_2$ ratios to be maintained in the liquid phases forming during the process, no such differences manifest themselves in the gas phases coming into contact with said liquid phases, and that, provided the molar $NH_3/CO_2$ ratio in the gas remains between 1:1 and 6:1, the desired molar $NH_3/CO_2$ ratios in the liquid phases will be estabished automatically. Thus, by maintaining a molar $NH_3/CO_2$ ratio of 1:1 to 6:1 in the gas phase issuing from the top of the urea formation reactor, the composition of the urea solution in contact with said gas phase will be automtically maintained such that the molar $NH_3/CO_2$ ratio in said solution will be approximately between 3:1 and 6:1. Similarly, if the molar $NH_3/CO_2$ ratio in the gases from the ammonium carbamate reactor is maintained between 1:1 and 6:1, the molar $NH_3/CO_2$ ratio in the carbamate melt will likewise be between 2:1 and 3:1.

The process therefore can be controlled according to this invention by maintaining the molar $NH_3/CO_2$ ratios in each of the gas phases within the range 1:1 and 6:1. To achieve optimum temperature conditions in the process, it has also been found the molar $NH_3/CO_2$ ratio in the gas phases must be kept within more narrow limits, e.g. within about 1.5:1 and 3.5:1.

DESCRIPTION OF FIG. 2, ILLUSTRATING THE INVENTION

Figure 2:
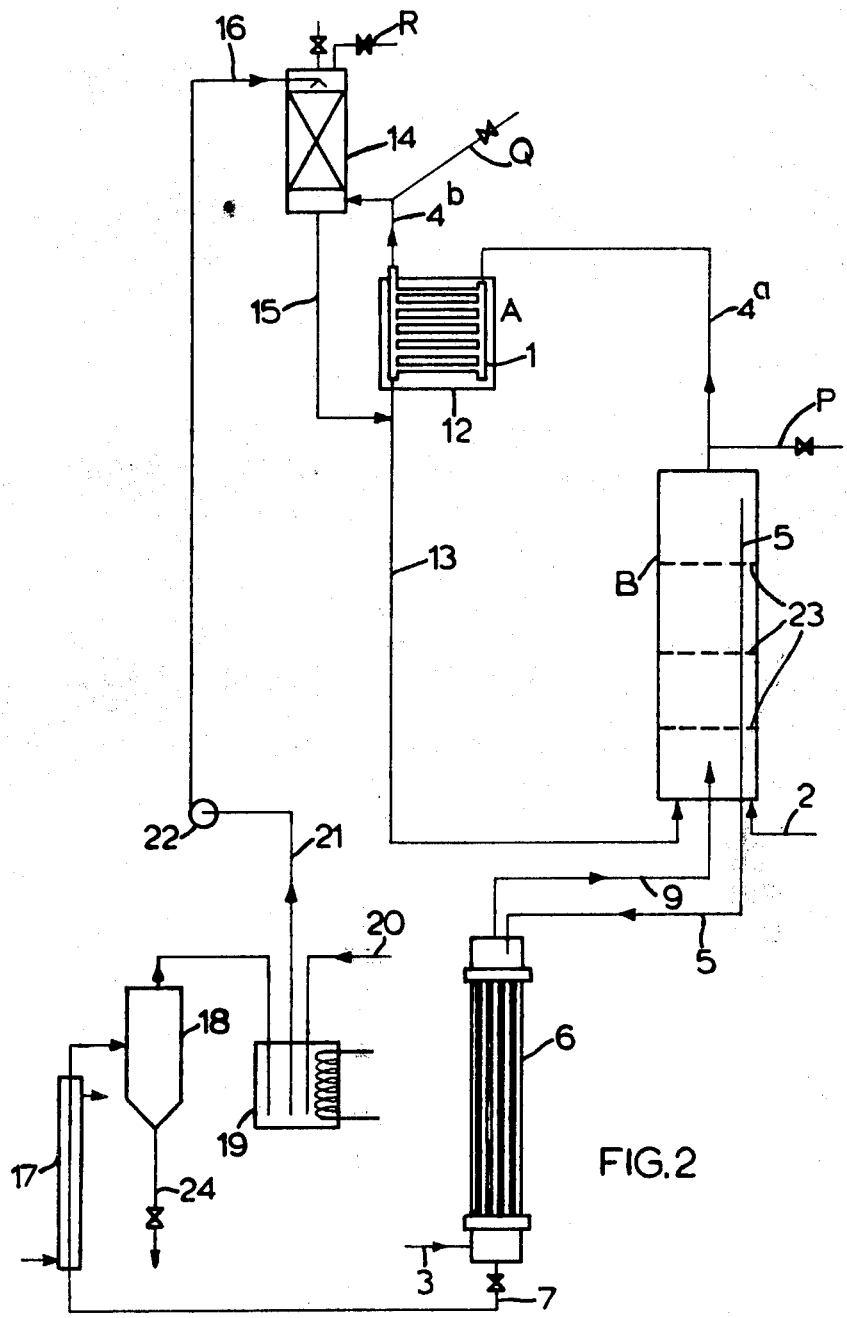

The method according to this invention is shown in the plant of flowsheet schematically illustrated in FIG. 2. This flowsheet shows similarities to that illustrated in FIG. 1, but the inert gases are now vented via a washing column connected to the carbamate reactor; further a low-pressure stage is shown and arranged so that the urea solution discharged from the base of the stripping column is further freed of dissolved ammonia and carbon dioxide with formation of a carbamate solution which is then recycled. In this flowsheet of FIG. 2, the urea solution formed in urea formation autoclave B flows via conduit (5) into stripping column (6) where it is stripped under high pressure with $CO_2$ fed to the base of stripper column (6) via conduit (3).

The gas mixture leaving the stripping column, mainly composed of $NH_3$ and $CO_2$, is introduced into the base of the urea formation autoclave via conduit (9). Ammonia, preferably in the liquid stage, is also supplied to the urea formation autoclave, via conduit (2). In the urea formation autoclave the feed gases bubble upward through the liquid phase, being partly dissolved on their way up, the non-dissolved portion being fed into tube system (1) of carbamate reactor A via conduit (4a). This carbamate reactor includes a pressure vessel (12) in which the tube system (1) is cooled by water. Owing to the strongly exothermic character of the ammonium carbamate forming reactor steam is generated in this water jacket.

The ammonium carbamate melt thus formed passes via conduit (13) to urea formation autoclave B wherein urea is gradually formed from it, with simulataneous release of water. In order that the urea autoclave functions as a series of continuous stirred tank reactors the autoclave is preferably divided into a number of superposed compartments by means of sieve plates (23), as shown.

The gases that have not been condensed to ammonium carbamate in the ammonium carbamate reactor, i.e., the inert gases, and $NH_3$ and $CO_2$, are led to a washing column (14) via conduit (4b), and the solution formed in said column is returned to the base of the urea formation column via conduits (15) and (13). The gases to be vented are discharged from the top of washing column (14).

The urea solution withdrawn from the base of stripping column (6) is expanded to about 4 absolute atmospheres, indirectly heated with steam in heater (17) so that any still-dissolved unreacted $NH_3$ and $CO_2$ gas is expelled, and thereafter a liquid-gas separation is effected in separator (18). The urea solution then formed is discharged via conduit (24) to be further processed to urea cyrstals or urea prills, as desired.

The gases are fed to a condensor (19) to be condensed to a carbamate solution by means of water and/or ammonia supplied via conduit (20), the heat of condensation being carried away by a cooling coil in the condensor. The liquid produced in this condensor passes via conduit (21), pump (22) and conduit (16) to the top of washing column (14) to be used as washing liquid.

For the purpose of analysis and control of the system, according to this invention, two sample-collecting pipes are also provided, i.e., a sampling pipe P in conduit (4a) for analyzing the gas phase flowing from urea formation column B and a sampling pipe Q in conduit (4b) for analyzing the gas phase from the carbamate reactor. The sampling pipes P and Q are connected e.g. with gas chromatographs (not shown). Pipe R is provided with a volume meter to control the vent gas volume (the vent gases consist mainly of inert gases, which are continuously supplied to the system mainly as impurities in the $CO_2$ feed).

The supply of ammonia and/or carbon dioxide to the system is now controlled on the basis of the gas phase analysis as indicated above. If the composition of the gas phase is such that the molar $NH_3/CO_2$ in said phase is outside the range 1:1 to 6:1, the feed of $NH_3$ or $CO_2$ is accordingly increased or decreased to bring that ratio within the prescribed limits, so that the required reaction molar ratio will be established again in the liquid phases.

Practice has shown that a satisfactory control can be achieved merely by sampling only the gases issuing from the ammonium carbamate reactor (sampling point Q). If in another embodiment the ammoniumcarbamate reactor is arranged before the urea formation autoclave as shown in FIG. 1, a satisfactory control can be achieved merely by sampling only the gases issuing from the urea formation autoclave and ajusting the supply of $NH_3$ to the autoclave via conduit 2a.

In the process as illustrated in the flowsheet of FIG. 2, the urea solution discharged from the urea formation autoclave is subjected to a stripping treatment with $CO_2$ gas flow under a high pressure. This stripping treatment could also be carried out with $NH_3$ or with a mixture of $NH_3$ and $CO_2$, of course, but this alternative is less attractive for economic reasons, although the principles and practice according to this invention would remain applicable in such a method.

It will be appreciated that in practicing the process of this invention as just described, the temperatures and pressures employed will be within the range of those which are already known to be effective in this art. The use of particular temperatures and pressures, etc., forms no part of this invention, which is, instead, directed to a means for the control of the reactants, and reacting media, as has been described However, as a matter of convenience, it is here further stated that the temperatures employed in the ammonium carbamate reactor will normally be in the range of about 155° to 170° C, and the corresponding pressures will be in the range of about 100 to 140 atm. Similarly, in the urea autoclave, the temperatures will be in the range of about 170° to 190° C, and the pressures in the range of about 100 to 140 atm. In the stripping column, it has already been mentioned that carbon dioxide gas is supplied under a high pressure to effect the removal of the gaseous components from the countercurrent-flowing liquid, and the pressures thus utilized may be in the range of about 100 to 140 atm., the temperatures existing within the steam heated shall of the stripping column being in the range of about 180° to 230° C.

This invention may accordingly be practiced in accordance with the principles illustrated and described hereinabove and is not limited to any specific embodiment, but only by the spirit and scope of the following claims.

What is claimed is:

1. In continuous processes for producing urea which comprise (1) reacting $NH_3$ and $CO_2$ at a pressure of 100–140 atm. and a temperature of 155°–170° C to form initially an ammonium carbamate solution (2) subsequently converting said solution at a pressure of 100–140 atm. and a temperature of 170°–190° C into a urea solution which contains ammonium carbamate and/or dissolved $NH_3$ and $CO_2$, (3) thereafter stripping the said urea solution with a member selected from the group consisting of $NH_3$, $CO_2$ and mixtures thereof, whereby a large part of the unreacted $NH_3$ and $CO_2$ and the additional $NH_3$ and $CO_2$ from the decomposition of the unconverted ammonium carbamate present in said solution is removed therefrom in the gaseous state, (4) feeding the stripped $NH_3$ and $CO_2$ to the ammonium carbamate-formation zone or the urea-formation zone, (5) expanding the resulting urea solution to a low pressure to effect further removal of still dissolved $NH_3$ and $CO_2$, (6) removing the urea solution freed of dissolved $NH_3$ and $CO_2$ for further processing, the improvement wherein there is maintained (a) in the ammonium carbamate-formation zone a value of from 2:1 to 3:1 for the $NH_3/CO_2$ molar ratio of the $NH_3$ and $CO_2$ bonded otherwise than in the form of urea and biuret, and (b) in the urea-formation zone, a value of from 3:1 to 6:1 for the $NH_3/CO_2$ molar ratio of the $NH_3$ and $CO_2$ present in the liquid phase as such and as $NH_3$ and $CO_2$ bonded otherwise than in the form of urea and biuret, by continual sensing and analysis of the molar $NH_3/CO_2$ gas ratio in one of the gas phases that are in contact with the liquid phases in said respective zones, and controlling the supply of $NH_3$ and/or $CO_2$ so as to maintain the thus-sensed said gas ratio within the range of 1:1 to 6:1, whereby the said $NH_3/CO_2$ ratios in the respective said liquid phases, and the desired temperatures in the said respective zones are thereby maintained.

2. A process according to claim 1 in which the molar ratio of $NH_3$ to $CO_2$ in the said gas phases is kept within the range from 1.5:1 to 3.5:1.

* * * * *

UNITED STATES PATENT OFFICE
CERTIFICATE OF CORRECTION

Patent No. 4,001,320  Dated January 4, 1977

Inventor(s) Petrus J. C. Kaasenbrood

It is certified that error appears in the above-identified patent and that said Letters Patent are hereby corrected as shown below:

Claim 1, line 24, after "$CO_2$" insert:

--present in the liquid phase as such and as $NH_3$ and $CO_2$--.

Signed and Sealed this

Third Day of May 1977

[SEAL]

Attest:

RUTH C. MASON
Attesting Officer

C. MARSHALL DANN
Commissioner of Patents and Trademarks